United States Patent [19]
Thein

[11] Patent Number: 5,356,435
[45] Date of Patent: Oct. 18, 1994

[54] ELEMENT FOR FIXING LIGAMENTS

[75] Inventor: Rafael Thein, Rehovot, Israel

[73] Assignee: Cendis Medical, Paris, France

[21] Appl. No.: 9,932

[22] Filed: Jan. 27, 1993

[51] Int. Cl.5 .............................................. A61F 2/08
[52] U.S. Cl. ........................................ 623/15; 623/18
[58] Field of Search ............... 623/13, 16, 18; 606/73, 606/72, 60

[56] References Cited

U.S. PATENT DOCUMENTS

| 4,772,286 | 9/1988 | Goble et al. | 623/13 |
| 4,828,562 | 5/1989 | Kenna | 623/13 |
| 4,955,910 | 9/1990 | Bolesky | 623/13 |
| 5,108,431 | 4/1992 | Mansat et al. | 623/13 |

FOREIGN PATENT DOCUMENTS

| 0278713 | 8/1988 | European Pat. Off. . |
| 0330328 | 8/1989 | European Pat. Off. . |
| 0358372 | 3/1990 | European Pat. Off. . |
| 2586927 | 9/1986 | France . |
| 2622430 | 11/1987 | France . |

*Primary Examiner*—David Isabella
*Attorney, Agent, or Firm*—Bacon & Thomas

[57]     ABSTRACT

An element for fixing a ligament adapted to be inserted in an osseous canal comprising an at least partially hollowed truncated element including an internal conduit adapted to receive one of the end sections of a ligament. A fastening member is provided that extends through the truncated element and clamps the respective end section of the ligament inside the conduit.

6 Claims, 1 Drawing Sheet

5,356,435

ELEMENT FOR FIXING LIGAMENTS

BACKGROUND OF THE INVENTION

The present invention relates to an element for fixing ligaments.

The grafting of natural ligaments or the placing of artificial ligaments is generally effected by previously making in the opposite osseous bodies canals in which the ends of the ligaments are introduced and fixed.

However, taking into account the efforts to which they are subjected, the ligaments tend to rupture, loosen or slacken to such an extent that it becomes necessary to operate again to replace or re-tension them.

In the case of conventional modes of fastening (screws, clips, . . . ), the operations prove to be delicate and the results are not always satisfactory.

SUMMARY OF THE INVENTION

It is an object of the present invention to solve these problems or at least to attenuate them.

This object is attained by means of an element for fixing ligaments adapted to be inserted in an osseous canal, comprising an at least partially hollowed truncated element provided with an internal conduit adapted to receive one of the end sections of the ligament and structure for clamping the section inside the conduit. The height of the element being such that its widened end lies outside the canal and according to an advantageous characteristic, the clamping structure comprise a threaded rod moving in a tapping formed in inclined manner through the truncated element, opening, outside the canal, on the lateral wall of the element and, inside, in the internal conduit.

According to another characteristic, the internal conduit is inclined with respect to the axis of the truncated element.

According to yet another characteristic, the internal conduit comprises a widened zone located in line with the tapping.

The fixing element according to the invention makes it possible easily to re-tension slackened ligaments without it being necessary to modify the implantation thereof.

BRIEF DESCRIPTION OF THE DRAWINGS

The present invention will be more readily understood on reading the following description with reference to the accompanying drawings, in which.

DETAILED DESCRIPTION OF THE PREFERRED EMBODIMENTS

Figure 1:
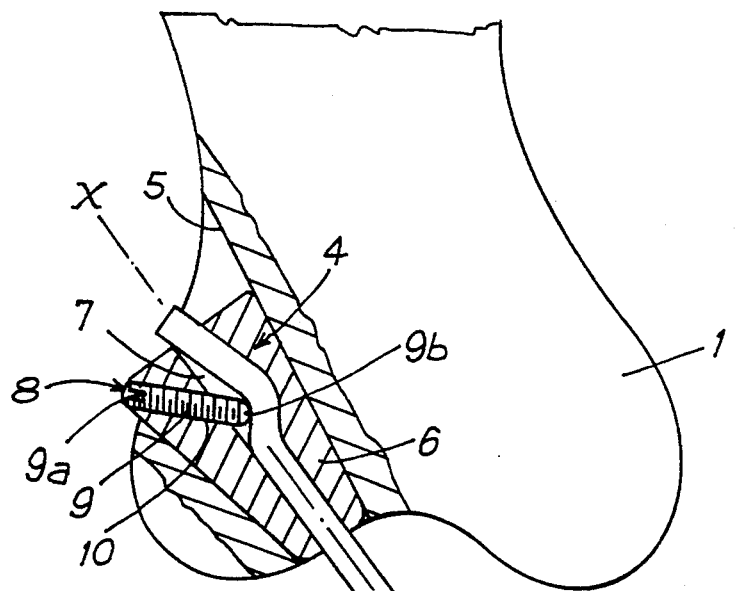
FIG. 1 shows a view in section of a first embodiment of the invention illustrated by two fixing elements implanted respectively in two osseous bodies joined by a ligament.

FIG. 1 shows two osseous bodies 1, 2 joined by a ligament 3. The ligament 3 is placed by means of the fixing elements 4 which are implanted in canals 5 made through the osseous bodies 1, 2. Elements 4 are constituted by at least partially hollowed conical frustums 6 provided with an internal conduit 7 adapted to receive one of the end sections of the ligament 3.

The canals 5 are made over a length shorter than the height of the element 4 so that the widened end of the element 4 lies outside the canal 5.

The truncated shape of elements 4 allows them to be blocked in the canals 5 by their outer face abutting against the inner wall of the canals 5. In order to avoid deterioration of the canals 5, the narrow end of the truncated element 4 is preferably made with rounded edges. Elements 4 also comprise means 8 for clamping the end sections of the ligament 3 inside the internal conduit 7.

In the embodiment of FIG. 1, the internal conduit 1 is straight, with dimensions slightly larger than those of the ligament and along the longitudinal axis X of element 4. The clamping means 8 advantageously comprise a threaded rod 9 moving in a tapping 10 made in inclined manner through element 4, oriented towards its longitudinal axis. The tapping 10 therefore opens, outside, on the lateral wall of element 4 and, inside, in the internal conduit 7.

The height of element 4 and the length of canal 5 are coordinated in order that the tapping 10 opens on a part of element 4 located outside canal 5 so that the end of the rod 9 is accessible.

It is advantageously provided to make a recess 11 on the inner wall of conduit 7 to create a widened zone located opposite the opening of the tapping 10. In this way, when the end section of the ligament is in place in conduit 7, the threaded rod 9 is driven in, its head comprising a screwing groove 9a and its inner end being shaped as a point 9b. The point 9b then crushes the ligament in order to block it in conduit 7. Under the pressure of the rod 9, the ligament 3 is deformed and fills the recess 11, taking a bent shape.

In an advantageous embodiment of the invention, the diameter of the truncated element 4 at its narrow end is less than or equal to 5 mm and is less than or equal to 8 mm at its wide end.

According to an embodiment (not shown), the internal conduit 7 is inclined with respect to axis X of element 4.

Figure 2:
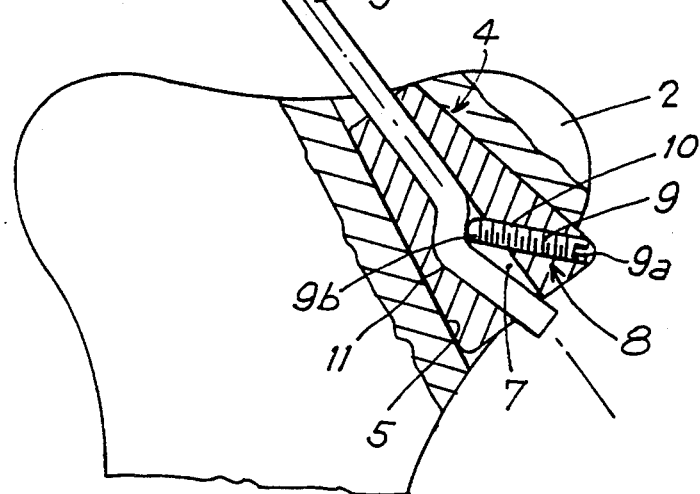
FIG. 2 shows a view in section of a second embodiment of the invention.
Figure 2:
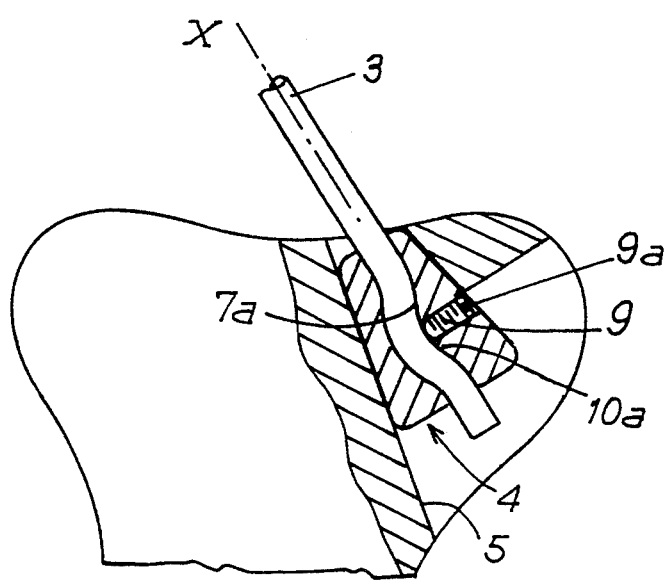

According to the embodiment of FIG. 2, the internal conduit comprises a bent part 7a located substantially at the level of the inner opening of the tapping 10. Tapping 10 comprises an inner extension 10a forming the concave zone of the bent part 7a and is made perpendicularly to axis X of element 4, it being ensured that the end of the rod 9 remains accessible outside the osseous canal 5. This latter embodiment reinforces the holding of the ligament 3 in element 4 by increasing the surfaces in contact between the ligament and the wall of the internal conduit 7.

I claim:

1. An element for fixing a deformable ligament within an osseous canal comprising:

a truncated conical element including a first diametric end portion and a second, widened diametric end portion, said truncated conical element being adapted to be received within an osseous canal with at least part of said second, widened diametric portion projecting outside the osseous canal, said truncated conical element being formed with an internal conduit defining a longitudinal axis and which is adapted to receive a deformable end of a ligament, said internal conduit including a widened zone defined by a recessed segment, said truncated conical element also being formed with a threaded bore opening at the part of said second widened diametric end portion projecting outside the osseous canal and opening into said internal conduit, said bore being inclined with respect to said longitudinal axis and opening into sad internal conduit at a position opposite the recessed segment of said internal conduit; and a threaded fastener positioned within said bore, said fastener having a first end that is accessible form outside said bore and a second end that is adapted to be shifted toward said recessed segment whereby, upon insertion of a deformable end of a ligament within said internal conduit, said fastener can be threaded within said bore such that the second end of said fastener engages the ligament to cause the ligament to deform so as to fill said recessed segment by taking a bend shape thereby retaining the ligament within said internal conduit.

2. An element according to claim 1, wherein the first diametric end portion of said truncated conical element is rounded edges.

3. An element according to claim 1, wherein said recessed segment is defined by a bent section of said internal conduit.

4. An element according to claim 1, wherein the first diametric end portion of said truncated conical element has an associated diameter less than or equal to 5 mm.

5. An element according to claim 4, wherein the second, widened diametric end portion of said truncated conical element has an associated diameter less than or equal to 8 mm.

6. An element according to claim 1, wherein the first end of said threaded fastener defines a head having a screwing groove formed therein and the second end of said threaded fastener is tapered.

* * * * *